United States Patent [19]

Arnold

[11] 4,287,415
[45] Sep. 1, 1981

[54] MEASUREMENT OF FLOWING WATER SALINITY WITHIN OR BEHIND WELLBORE CASING

[75] Inventor: Dan M. Arnold, Houston, Tex.
[73] Assignee: Texaco Inc., White Plains, N.Y.
[21] Appl. No.: 126,754
[22] Filed: Mar. 3, 1980
[51] Int. Cl.³ ............................................. G01V 5/00
[52] U.S. Cl. ................................................. 250/270
[58] Field of Search ....................... 250/270, 269, 266

[56] References Cited

U.S. PATENT DOCUMENTS

| | | | |
|---|---|---|---|
| 3,930,154 | 12/1975 | Scott | 250/270 |
| 4,032,778 | 6/1977 | Paap et al. | 250/270 |
| 4,032,779 | 6/1977 | Arnold et al. | 250/270 |
| 4,032,780 | 6/1977 | Paap et al. | 250/270 |
| 4,051,368 | 9/1977 | Arnold et al. | 250/270 |
| 4,137,452 | 1/1979 | Paap et al. | 250/270 |
| 4,151,413 | 4/1979 | Arnold | 250/270 |

*Primary Examiner*—Davis L. Willis
*Attorney, Agent, or Firm*—Carl G. Ries; Robert A. Kulason; Jack H. Park

[57] ABSTRACT

Water flowing within or behind a wellbore casing is irradiated with 14 MeV neutrons. Gamma radiation from the isotope nitrogen 16 induced from the $O^{16}(n,p)N^{16}$ reaction and either the $Na^{23}(n,\alpha)F^{20}$ or the $Cl^{37}(n,\alpha)P^{34}$ reaction is measured in intensity and energy with detectors in a downhole sonde. From the gamma radiation measurements, the salinity of water flowing either within or behind wellbore casing may be determined.

10 Claims, 5 Drawing Figures

4,287,415

MEASUREMENT OF FLOWING WATER SALINITY WITHIN OR BEHIND WELLBORE CASING

BACKGROUND OF INVENTION

1. Field of Invention

The present invention relates to nuclear well logging to determine the salinity of water flowing either within or behind casing in a well borehole.

2. Description of Prior Art

U.S. Pat. Nos. 4,032,778; 4,032,779 and 4,032,780 of common ownership describe techniques for measuring water flow within or behind wellbore casing. The flowing water is irradiated with 14 MeV neutrons produced in an accelerator in a downhole sonde. The radioactive isotope nitrogen 16 induced in water through the $O^{16}(n,p)N^{16}$ reaction is measured in energy and intensity with two detectors in the sonde so that the direction, linear flow velocity, volume flow rate and radial position of the center of water flow can be detected.

When water channels behind casing in the vicinity of the well borehole, it is of interest to define both the zone or zones from which the water is flowing and the zone or zones into which the water flows. Where the distance of the center of the flow channel is less than the maximum depth of investigation from the sonde, usually on the order of eight inches or so, the flow source zone can be located and flow can be usually followed. However, there are also situations where the entry or exit point of channeling water is outside of the maximum depth of investigation. Identification of the source of channeling water is of interest to a reservoir engineer.

SUMMARY OF INVENTION

Briefly, the present invention provides a new and improved method for determining the salinity of a fluid flowing within or behind a casing in a well borehold so that the source of the water may be determined. A well tool which has a source of high energy neutrons and at least one gamma ray detector longitudinally spaced from the source are mounted in a sonde which is moved in the borehole to formations of interest which are to be measured and tested for fluid flow. The sonde is configured such that the water flows first past the high energy neutron source and then past the gamma ray detector(s) (See U.S. Pat. Nos. 4,032,778; 4,032,779; 4,032,780). The source irradiates the borehole environs with high energy neutrons to cause the nuclear activation reaction $O^{16}(n,p)N^{16}$ and the nuclear activation reactions $Na^{23}(n,\alpha)F^{20}$ and $Cl^{37}(n,\alpha)P^{34}$ to occur. Gamma radiation caused by the decay of unstable isotopes from these nuclear reactions is detected and representative signals are formed based on the detected gamma radiation. A measure of the relative presence of oxygen and either sodium or chlorine in the fluid in the vicinity of the detector(s) is then obtained from the detected gamma rays, and from the measure an indication of the salinity is formed so that the source of the water may be determined.

DESCRIPTION OF PREFERRED EMBODIMENT

Figure 1:
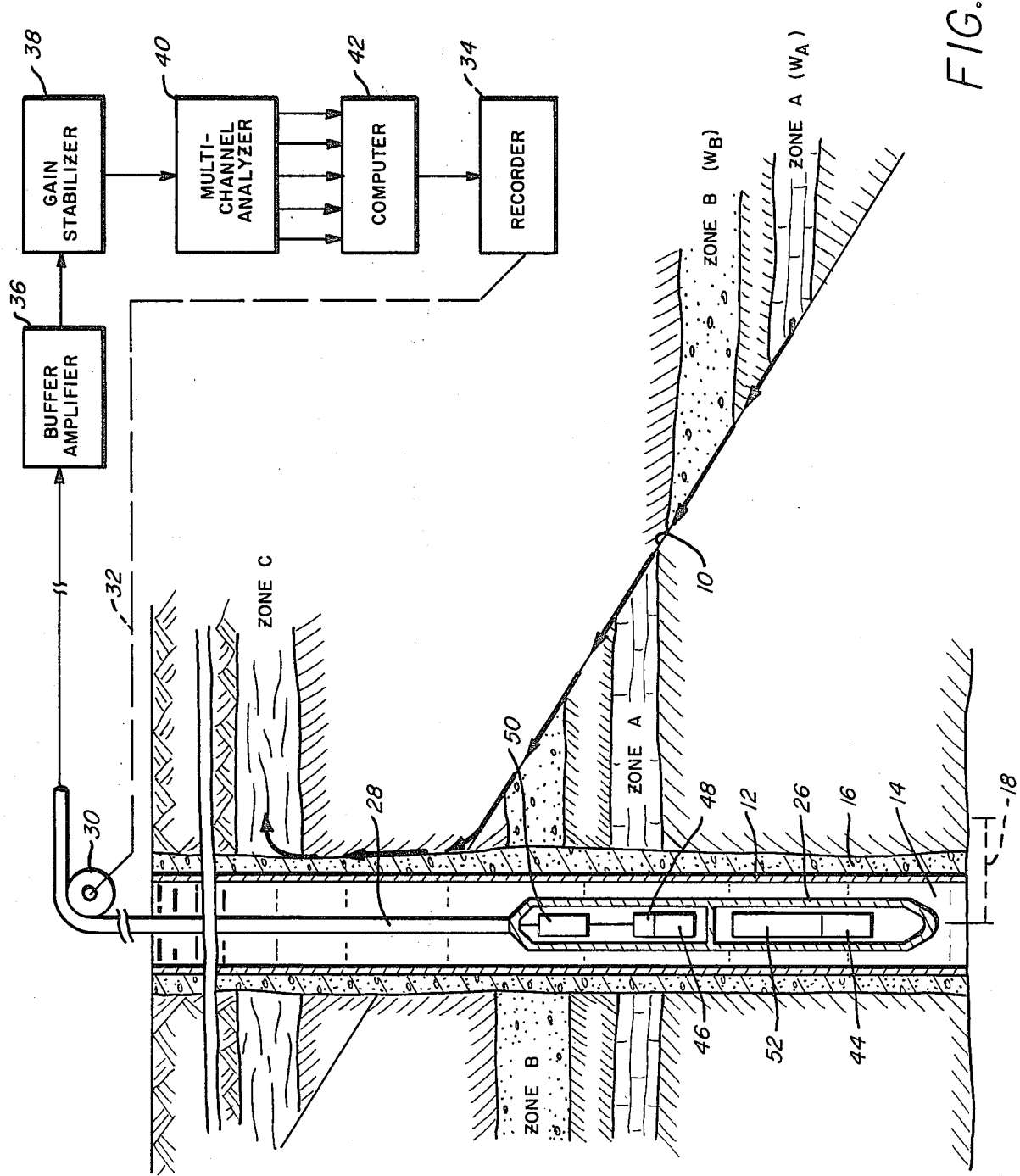
FIGS. 1 and 2 are schematic drawings of water salinity detection system in well bores according to the present invention, only one gamma ray detector being shown.

In the drawings (FIG. 1), water of salinity $W_A$ is illustrated schematically as flowing from a formation or zone A up a fault plane 10. In the vicinity of a casing 12 surrounding a well borehole 14, the flowing water channels upward behind the casing 12 and cement 16 and enters zone C, as indicated by arrows. Zone A, the source of the flow, as well as Zone B having water with a salinity $W_B$, are outside the maximum depth of investigation, as indicated by a phantom line 18, utilizing the flow measurement techniques of the prior art patents of common ownership previously discussed. Thus, there is no way using the techniques of these patents of identifying whether zone A or zone B is the source of the channeling water. As has been previously discussed, there are situations where this information is of interest to a reservoir engineer.

Figure 2:
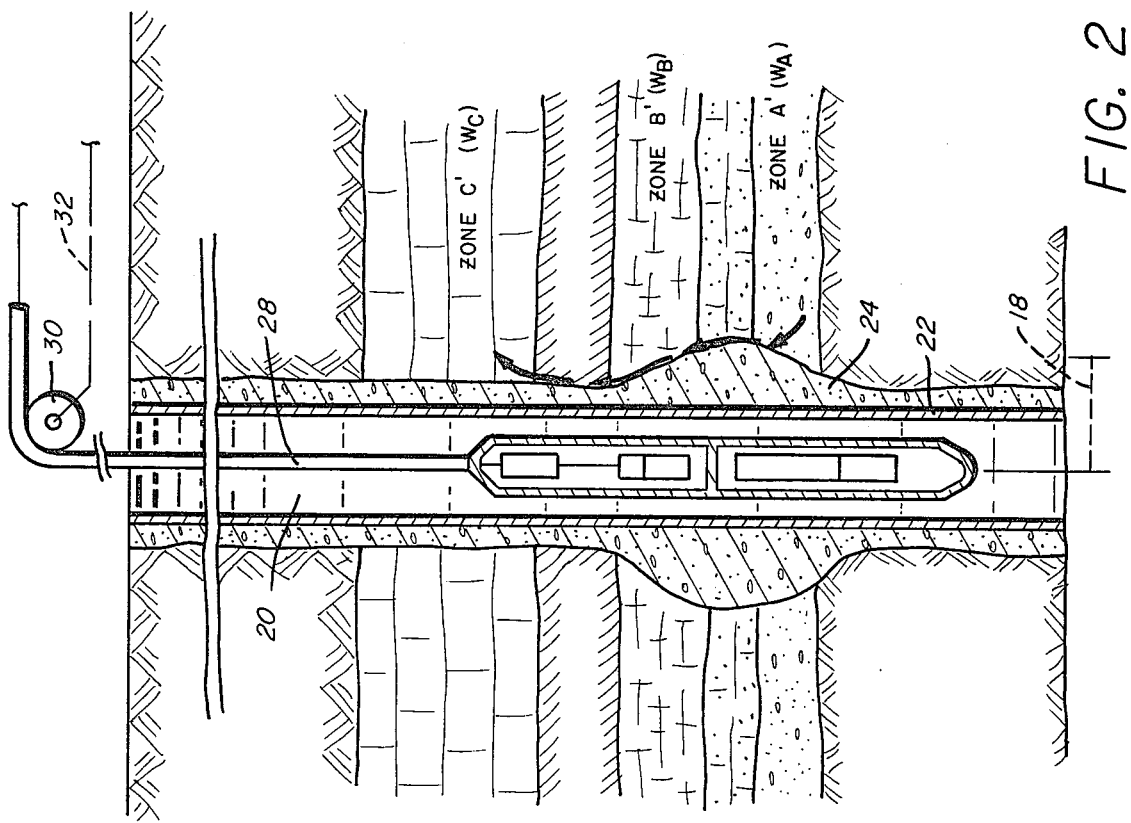

Another example situation which occurs is shown in FIG. 2. A borehole 20 surrounded by a casing 22 and cement 24 is badly washed out across zones A' and B'. As indicated by arrows, water is flowing from zone A' into C'. Again, however, the point of entry of the water from the zone A' is outside the maximum depth of investigation, so that prior art flow measurement techniques discussed above could not identify zone A' as the source of water.

Referring now to FIGS. 1 and 2, a salinity measuring system for water flowing within or behind the casing 12 (FIG. 1) or 22 (FIG. 2) in accordance with the present invention is shown schematically. A downhole sonde 26 is shown suspended by a well logging cable 28 in the well borehole 14 or 20 which is filled with borehole fluid and surrounded by earth formations which include either the water flow zones A, B, C of FIG. 1 or the flow zones A', B' and C' of FIG. 2.

The well logging cable 28 passes over a sheave wheel 30 which is mechanically or electrically coupled, as indicated by a dotted line 32, to a recorder 34 so that measurements obtained from signals recrived via cable 28 from the downhole sonde 26 may be recorded as a function of depth in the well borehole 14 or 20. The received signals are formed in the sonde 26 in a manner to be set forth and pass through a conventional buffer amplifier 36 and gain stabilizer 38 to a pulse height analyzer 40. The pulse height analyzer may be either a multi-channel analyzer or a plurality of single channel analyzers appropriately biased to receive and count pulses received in certain preselected energy windows, as will be set forth.

The pulse counts from analyzer 40 are furnished to a digital computer 42, such as a PDP-11 computer, which obtains measures of the relative presence of certain chemical elements in the vicinity of the sonde 26, and therefrom a measure or indication of the salinity of water flowing behind the casing 12 or 20 so that the formation which is the source of such flowing water may be determined.

Housed in the downhole sonde 26 is a neutron source 44 which may be a continuous chemical or accelerator type neutron source producing high energy neutrons having an energy level for some, at least, of ten MeV or greater. For best results, the neutron source 44 should be a pulsed, accelerator type producing essentially monoenergetic fourteen MeV neutrons (see prior art patents of common ownership previously discussed).

Spaced a suitable distance from the neutron source 44 is a gamma ray scintillation detector 46. The detector comprises a sodium iodide (thallium activated) crystal or a cesium iodide (thallium activated) crystal of suitable size and shape. The scintillation crystal of detector 46 is optically coupled through a photomultiplier tube 48 which functions to count scintillations or light flashes occurring in the crystal from impingement thereon by high energy gamma rays from radioactive materials in the vicinity of the sonde 26.

As is known, the voltage pulses produced by the photomultiplier 48 are proportional in height to the energy of the gamma rays impinging upon the crystal of the detector 46. Thus, the detector 48 forms a succession of pulses proportional in height to the energy of the impinging gamma rays which is then coupled through suitable conventional amplifiers and electronics 50 to the surface pulse height analyzer 40 via a conductor of the well logging cable 28. Appropriate power sources (not shown) are supplied at the surface and connected to the downhole electronic equipment via other conductors of the cable 28 in order to provide operating power.

Although not essential, best results are obtained by pulsing the neutron source 44 and gating the detector 46 "on" approximately three milliseconds after termination of the neutron pulse. This pulse-delay-detection sequence allows interfering thermal capture gamma radiation to decay to a negligible level before the desired, longer lived, gamma radiations from the activation reactions are detected (see prior art patents of common ownership previously discussed).

Spaced between the neutron source 44 and the detector 46 in the downhole sonde 18 is shielded by a shielding material 52 of a suitable type to prevent direct irradiation of the detector crystal 46 with neutrons from the neutron source 44. Shielding materials with high hydrogen content such as paraffin or other poly-molecular hydrocarbon structure may be utilized for this purpose. Further, strong thermal neutron absorbers such as cadmium may be interposed in layers within the hydrogenate shielding material in order to make up the shield portion 52.

In logging operations, the sonde 26 is moved through the borehole and positioned within the zone in which the fluid is flowing directly behind or within the borehole casing. As an illustration, assume that salt water is flowing upward behind the casing. For upward flow, the sonde is configured such that the neutron source 44 is below the gamma ray detector 46 as discussed in prior art patents of common ownership.

As the salt water flows past neutron source 44, the radioactive isotopes $N^{16}$, $F^{20}$, and $P^{34}$ are induced within the water by the fast neutron activation reactions $O^{16}(n,p)N^{16}$, $Na^{23}(n,\alpha)F^{20}$, and $Cl^{37}(n,\alpha)P^{34}$, respectively. $N^{16}$, $F^{20}$, and $P^{34}$ decay by the emission of gamma radiation of characteristic energy with half lives of 7.36 sec, 10.7 sec, and 12.4 sec, respectively. Unless the flow is extremely slow, there are measurable levels of $N^{16}$, $F^{20}$, and $P^{34}$ remaining in the water as it moves from the vicinity of the source 44 to the vicinity of the detector 46.

Figure 3:
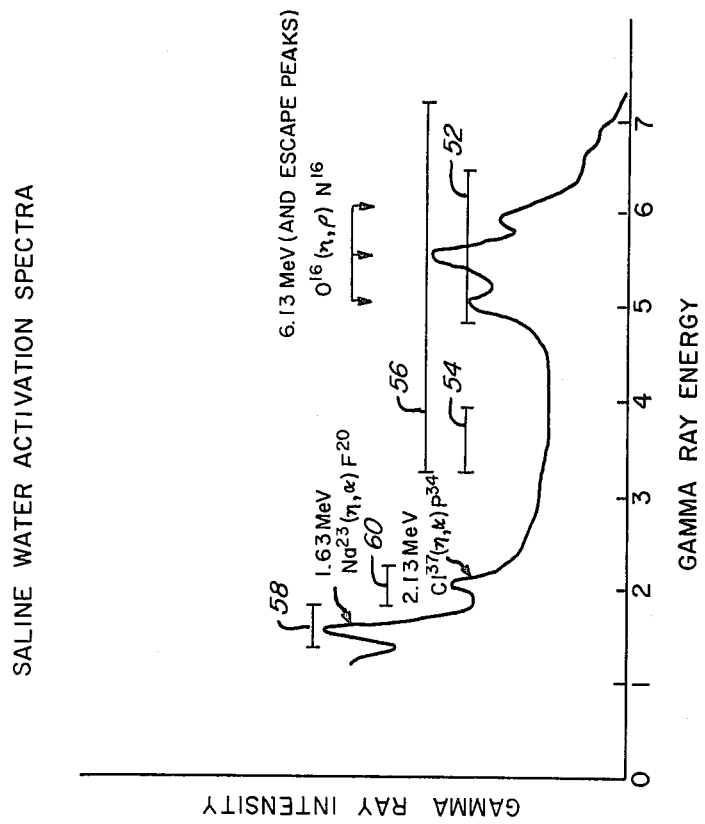
FIG. 3 is a graphical representation of typical gamma radiation counts as a function of energy level obtained with the present invention.

Detector 46 detects induced activation radiation of the foregoing types and photomultiplier tube 48 forms electrical pulse signals in response to detection of gamma radiation. Signals from the downhole photomultiplier 48 are transmitted to the surface via the logging cable 20 and are provided the pulse height analyzer 40. In the pulse height analyzer 40, window 52 (FIG. 3) is set from approximately 4.9 to approximately 6.5 MeV. If flow measurement according to patents of common ownership previously discussed is desired, windows 54 and 56 are also set for the response of detector 46 and window 56 is set for the response of a second gamma ray detector (not shown) in accordance with such patents.

In addition, a suitable energy window is set for the response of detector 46 to detect either gamma radiation from the activation of sodium or chlorine. For example, a suitable energy window 58 is set from 1.45 to 1.80 MeV to detect $F^{20}$ peak at approximately 1.63 MeV. Alternatively, a window 60 is set from 1.80 MeV to 2.2 MeV so that the $P^{34}$ peak at approximately 2.13 MeV may be counted in the pulse height analyzer 40, for reasons to be set forth.

The computer 42 receives count rate signals from the pulse height analyzer 40 and processes such signals in a manner to be set forth, to determine the salinity of the flowing water so that the zone or formation which is the source of such water may be identified.

Correction of counting rates for background in the high energy windows 52, 54 and 56 is performed as in the previously discussed U.S. Patents of common ownership which are incorporated by reference. Briefly, the background count rates are measured in the subject windows with either the sonde 26 oriented such that the water flows first past the detector 46 and then the source 44 or alternatively in a formation similar to the zone of interest which has no flow behind the casing.

Correction of count rate in the low "sodium" window 58 will be discussed in the following section.

DETERMINATION OF WATER SALINITY $C_1$ and $C_2$ are defined as counting rates recorded in the detector 46 in the energy window 52, from 4.9 to 6.5 MeV, and the energy window 58 from 1.45 to 1.80 MeV, respectively. After background correction, $C_1$ and $C_2$ can be expressed as:

$$C_1 = f_1 V K_o(R) 4 \cdot \sinh(\lambda_1 a/2v) \cdot \sinh(\lambda_1 b/2v) e^{-\lambda_1 S/v} \quad (1)$$

$$C_2 = f_2 V K_{Na}(R) 4 \cdot \sinh(\lambda_2 a/2v) \cdot \sinh(\lambda_2 b/2v) e^{-\lambda_2 S/v} \quad (2)$$

where the subscripts 1 and 2 refer to the $O^{16}(n,p)N^{16}$ and $Na^{23}(n,\alpha)F^{20}$ reactions, respectively, and V = volume flow rate of water (in$^3$/sec)
$\lambda_i$ = decay constant of the $i^{th}$ activation product (sec$^{-1}$)
a = effective irradiation length of the water stream (inches)
b = effective detection length of the water stream (inches)
v = the linear velocity of the water flow (inches/sec.)
S = the source-near detector spacing (inches)
$K_o(R), K_{Na}(R)$ = constants depending upon the distance R from the center of the sonde to the center of the flow and the gamma ray energy produced by the $O^{16}(n,p)N^{16}$ and $Na^{23}(n,\alpha)F^{20}$ reactions, respectively.

$$f_1 = N_o \rho \sigma_1 a \phi_n G_1 / M \lambda_1 b \quad (3)$$

$$f_2 = N_o \rho \sigma_2 a \phi_n G_2 W / 1000 \, M' \lambda_2 b \tag{4}$$

where
- $N_o$ = Avogadro's number
- $\rho$ = density of the water
- $M$ = molecular weight of water
- $M'$ = molecular weight of NaCl
- $\phi_n$ = source neutron output (neutrons/cm²/sec)
- $G_i$ = a geometric and efficiency constant of the detector for radiation from the $i^{th}$ activation product
- $W$ = the salinity of the water in parts per thousand NaCl The terms $K_o(R)$ and $K_{Na}(R)$ can be expressed as:

$$K_o(R) = K_1(R) K_{o,2}(R) \tag{5}$$

$$K_{na}(R) = K_1(R) K_{Na,2}(R) \tag{6}$$

where
- $K_1(R)$ = a function depending upon R (see U.S. Pat. No. 4,032,780), the distance from the source to the element of water being activated
- $K_{2,o}(R), K_{2,Na}(R)$ = constants dependent upon the distance R from activated water element to the detector and the energy of gamma radiation produced by the $O^{16}(n,p)$ and $Na^{23}(n,\alpha)$ reactions, respectively.

Dividing equation (2) by equation (1), substituting equations (3) through (6), and solving for salinity W yields:

$$W = 1000 \frac{\sinh(\lambda_1 h_1 a/2v)\sinh(\lambda_1 b/2v)}{\sinh(\lambda_2 a/2v)\sinh(\lambda_2 b/2v)} \cdot \frac{G_1}{G_2} \cdot \frac{K_{2,o}(R)}{K_{2,Na}(R)} \frac{C_1 \, e^{-\lambda_1 S/v}[\sigma_1 \lambda_2 M']}{C_2 e^{-\lambda_2 S/v} \, \sigma_2 \lambda_1 M} \tag{7}$$

The terms in brackets on the right-hand side of equation (7) are known. The terms S, a, and b are either known or determined during calibration. R and v are measured as described in U.S. Pat. Nos. 4,032,778 and 4,032,780. $C_1$ and $C_2$ are measured by the pulse height analyzer 40. The equation (7) can, therefore, be solved in computer 42 for W, the water salinity, once $G_1/G_2$ and $K_{2,o}(R)/K_{2,Na}(R)$ are computed or measured through a calibration procedure.

Physically $G_1/G_2$ is the ratio of efficiency of the gamma ray detector to 6.13 MeV radiation compared to 1.63 MeV radiation. Efficiency curves for gamma ray scintillation detectors are available in the literature, such as in "Calculated Efficiencies of Cylindrical Radiation Detectors," S. H. Vegors, L. L. Marsden, and R. L. Heath, Sept. 1, 1958, O.T.S., U.S. Dept. of Commerce, Washington, D.C. (#DIO 16370).

Figure 4:
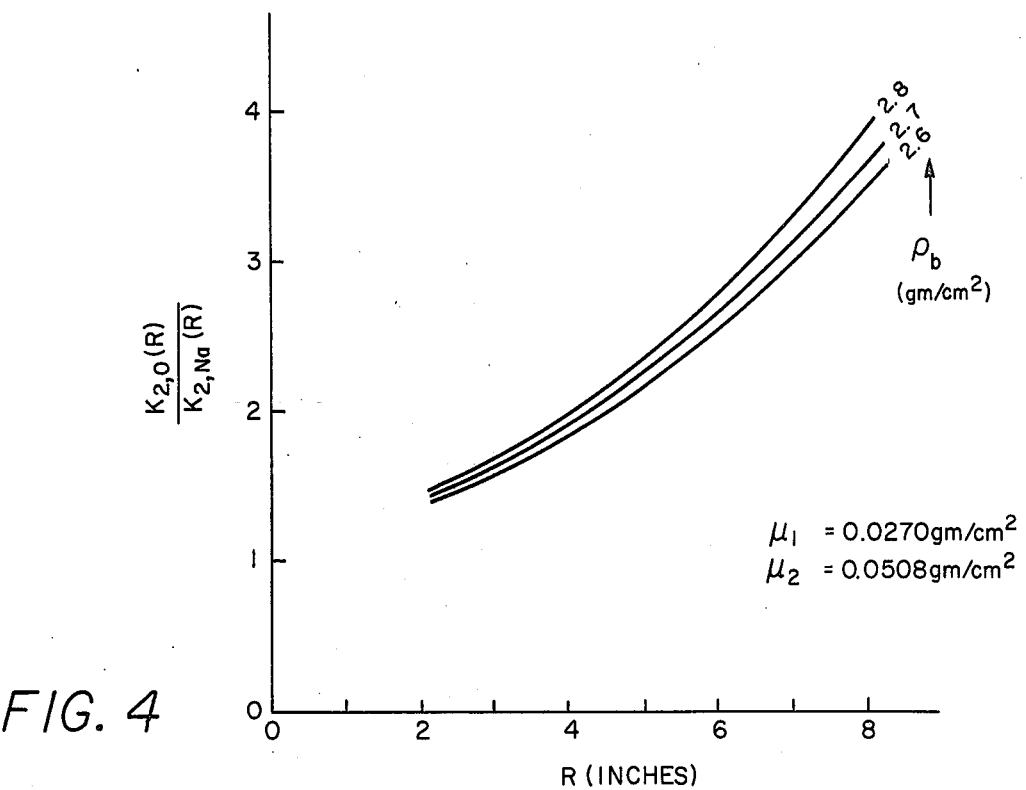
FIGS. 4 and 5 are graphical representations of calibrations constants empirically determined for use in the practice of the present invention.
Figure 5:
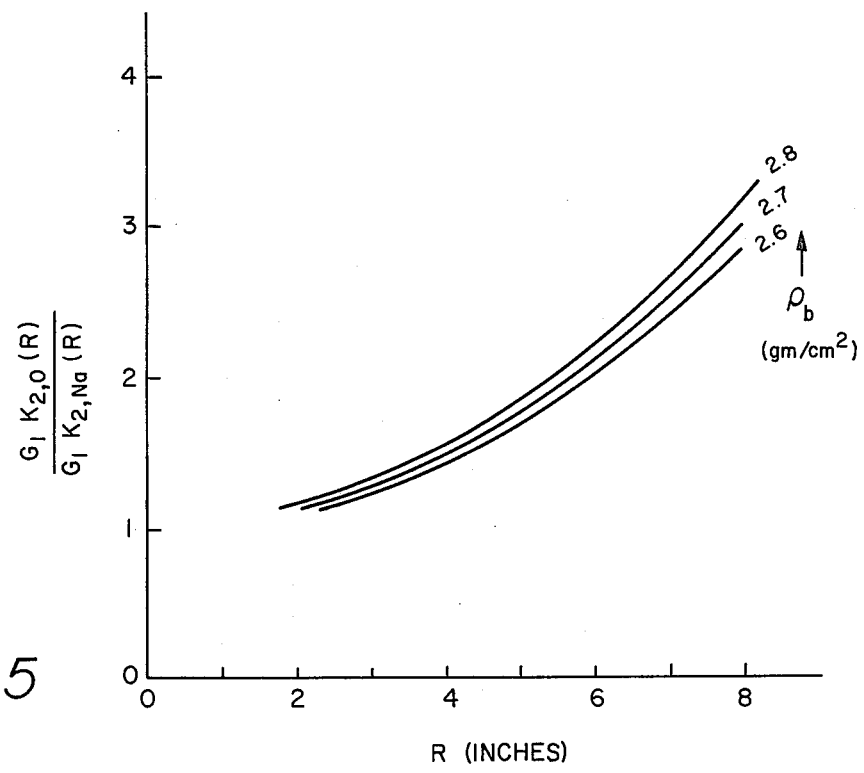

The ratio $K_{2,o}(R)/K_{2,Na}(R)$ is a function of the relative attenuation of 6.13 MeV to 1.63 MeV gamma radiation as the radiation travels from the irradiated water, through the intervening material (formation, cement annulus, wellbore casing, wellbore fluid, and sonde casing) of average bulk density $\rho_b$ to the detector. The ratio is of the general form:

$$K_{2,o}(R)/K_{2,Na}(R) \simeq e^{-2.54 R \rho_b (\mu_1 - \mu_2)} \tag{8}$$

where $\mu_1$ and $\mu_2$ are the known attenuation coefficients for 6.13 and 1.63 MeV radiation, respectively, in cm²/gm, $\rho_b$ is in grams/cm³, and R is in inches. FIG. 4 shows a plot of the ratio as a function of R with $\mu_1 = 0.0270$ gm/cm³ and $\mu_2 = 0.0508$ gm/cm³ for $\rho_b = 2.6, 2.7, 2.8$. Although $\rho_b$ is usually not known precisely, the composite value for most formation and borehole conditions varies between 2.6 and 2.8 gm/cm³. It can be seen that uncertainties in $\rho_b$ of $\pm 0.1$ gm/cm³ do not introduce excessive error in the ratio, especially if R<6 inches. Since R is measured, $\mu_1$ and $\mu_2$ are known, and $\rho_b$ can be estimated or obtained from known wellbore conditions and a formation density log, an approximate value of $K_{2,o}(R)/K_{2,Na}(R)$ can be obtained from equation (8). The product of the ratios $(G_1/G_2)[K_{2,o}(R)/K_{2,Na}(R)]$ as a function of R can also be measured using a calibration facility of the type where the sonde 26 is suspended in a tank of fresh water. Water of known salinity W is pumped through a pipe whose center is positioned R inches from the center of the sonde. Material of known density $\rho$ is positioned between the pipe and the detector 46. The linear flow velocity v through the pipe is known and controllable. The counting rates $C_1$ and $C_2$ are then measured. Equation (7) can then be solved for $(G_1G_2)[K_{2,o}(R)/K_{2,Na}(R)]$ since all other quantities are either measured or are known. Next R and/or $\rho$ is varied and the process is repeated. This procedure is continued until an empirical set of curves as shown in FIG. 5 is generated.

As mentioned previously, the count rate recorded in the low energy "sodium" window 60 must be corrected for background B. Background B consists of the sum of background components $B_1$, $B_2$, and $B_3$.

$B_1$ consists of background from naturally occuring radioactive elements within the formation, and from small contributions from $N^{16}$ resulting from activation of oxygen in the formation matrix. Background correction techniques in previously discussed U.S. patents of common ownership are suitable for measuring the magnitude of $B_1$.

$B_2$ consists of degraded 6.13 MeV and 7.12 MeV gamma radiation from $N^{16}$ induced in the flowing water by the fast neutron activation reaction $O^{16}(n,p)N^{16}$. $B_2$ can be expressed as:

$$B_2 = Z(R) \cdot C_1 \tag{9}$$

where $C_1$ is the count rate, corrected for background, recorded in the 4.9–6.5 MeV window and $Z(R)$ is a function of the shape of the $N^{16}$ spectrum which is, in turn, a function of R, the distance from the center of the sonde to the center of the flow. $Z(R)$ is measured during sonde calibration by flowing fresh water in the calibration facility where the sonde 26 is contained in a tank of water spaced by a material of known thickness and density from a pipe containing water of known flow rate. Since $C_1$ is measured by the pulse height analyzer 40, $Z(R)$ is a measured calibration function, and R is measured in accordance with U.S. Pat. No. 4,032,778 previously discussed, $B_2$ can be determined using equation (9).

$B_3$ consists of degraded 2.13 MeV gamma radiation from the $Cl^{37}(n,\alpha)P^{34}$ fast neutron activation reaction. Most chlorine, in earth formations, in contained in the formation water as NaCl. The "background" $B_3$ from $Cl^{37}(n,\alpha)P^{34}$ varies with the salinity of the flowing water. $B_3$ can, therefore, be considered as "signal" rather than background and does not have to be removed from the count rate $C_2$ recorded in the "sodium" window 60. The primary 2.13 MeV chlorine radiation can thus, in principle, be used instead of the 1.63 MeV radiation from sodium activation detected in window 58 to determine water salinity in the manner set forth above with appropriate adjustment for different calibration constants required due to the different counting windows used. The intensity of 2.13 MeV radiation is, however, less than that of the 1.63 MeV radiation (see FIG. 3).

In summary, the linear flow velocity v and the radial position R of the center of water flow are measured and determined in accordance with the techniques of U.S. Pat. Nos. 4,032,778 and 4,032,780. The calibration constants for the ratio of the efficiency of the gamma ray detector 46 to the 6.13 MeV gamma radiation to the 1.63 MeV gamma radiation and the calibration constant for the relative attenuation of the 6.13 MeV gamma radiation to the 1.63 MeV gamma radiation of equation (7) may be determined either from detector efficiency tables, gamma ray attenuation coefficients, known or estimated formation bulk density, and equation (8) or the empirical family of calibration curves of the type shown in FIG. 5.

The computer 42 then solves equation (7) for W, obtaining the salinity of the water flowing within or behind the wellbore casing 12 (or 20) based on the measured quantities $C_1$ and $C_2$. Since the salinity of the water from the various formations is known or may be determined in other sources in producing wells, the formation or zones serving as the source of such flowing saline water can be identified.

The foregoing disclosure and description of the invention are illustrative and explanatory thereof and various changes in the size, shape and materials as well as in the details of the preferred embodiment may be made without departing from the spirit of the invention.

I claim:

1. A method of determining the salinity of a fluid flowing within or behind a casing in a well borehole so that the source of such water may be determined, comprising the steps of:
   (a) locating a well tool having a source of high energy neutrons, at least some of which have sufficient energy to cause the nuclear reactions $O^{16}(n,p)N^{16}$ and $Na^{23}(n,\alpha)F^{20}$, and a gamma ray detector longitudinally spaced from the source, at a position in the well borehole;
   (b) irradiating the borehole environs with high energy neutrons from the source;
   (c) detecting gamma rays caused by the decay of the unstable isotopes nitrogen-16 and flourine-20 and generating signals respresentative thereof;
   (d) obtaining from the detected gamma rays a measure of the relative presence of oxygen and sodium in the fluid in the vicinity of the detector; and
   (e) obtaining from the measure of relative presence of oxygen and sodium an indication of the salinity of the fluid.

2. The method of claim 1, wherein said step of detecting includes: detecting gamma rays in the gamma ray spectrum in a preselected energy range corresponding to the decay of nitrogen-16.

3. The method of claim 2, wherein the preselected energy range extends from approximately 4.90 MeV to approximately 6.50 MeV.

4. The method of claim 1, wherein said step of detecting includes: detecting gamma rays in the gamma ray spectrum in a preselected energy range corresponding to the decay of flourine-20.

5. The method of claim 4, wherein the preselected energy range extends from approximately 1.45 MeV to approximately 1.80 MeV.

6. The method of determining the salinity of a fluid flowing within or behind a casing in a well borehole so that the source of such water may be determined, comprising the steps of:
   (a) locating a well tool having a source of high energy neutrons, at least some of which have sufficient energy to cause the nuclear reactions $O^{16}(n,p)N^{16}$ and $Cl^{37}(n,\alpha)P^{34}$, and a gamma ray detector longitudinally spaced from the source at a position in the well borehole;
   (b) irradiating the borehole environs with high energy neutrons from the source;
   (c) detecting gamma rays caused by the decay of the unstable isotopes nitrogen-16 and phosphorus-34 and generating signals representative thereof;
   (d) obtaining from the detected gamma rays a measure of the relative presence of oxygen and chlorine in the fluid in the vicinity of the detector; and
   (e) obtaining from the measure of relative presence of oxygen and chlorine an indication of the salinity of the fluid.

7. The method of claim 6, wherein said step of detecting includes: detecting gamma rays in the gamma ray spectrum in a preselected energy range corresponding to the decay of nitrogen-16.

8. The method of claim 7, wherein the preselected energy range extends from approximately 4.90 MeV to approximately 6.50 MeV.

9. The method of claim 6, wherein said step of detecting includes: detecting gamma rays in the gamma ray spectrum in a preselected energy range corresponding to the decay of phosphorus-34.

10. The method of claim 9, wherein the preselected energy range extends from approximately 1.8 MeV to approximately 2.5 MeV.

* * * * *